United States Patent [19]

Braatz et al.

[11] Patent Number: 5,462,536
[45] Date of Patent: Oct. 31, 1995

[54] PROTEIN NONADSORPTIVE MEMBRANES FOR WOUND DRESSINGS

[75] Inventors: James A. Braatz, Beltsville; Clifton L. Kehr, Silver Spring, both of Md.; Timothy G. Grasel, Calabasas, Calif.; William S. Letter, Columbia, Md.

[73] Assignee: Hampshire Chemical Corp., Lexington, Mass.

[21] Appl. No.: 91,532

[22] Filed: Jul. 14, 1993

Related U.S. Application Data

[63] Continuation of Ser. No. 825,361, Jan. 24, 1992, abandoned.

[51] Int. Cl.$^6$ .................. A61F 13/00; A61F 13/02
[52] U.S. Cl. .................. 604/304; 602/48; 602/50; 424/447; 424/448
[58] Field of Search .................. 604/304, 307, 604/890.1; 602/48, 50; 424/447, 448, 449

[56] References Cited

U.S. PATENT DOCUMENTS

| | | | |
|---|---|---|---|
| 3,719,050 | 3/1973 | Asao et al. | 405/264 |
| 3,903,232 | 9/1975 | Wood et al. | 264/157 |
| 3,939,123 | 2/1976 | Matthews et al. | 528/60 |
| 4,118,354 | 10/1978 | Harada et al. | 524/711 |
| 4,127,124 | 11/1978 | Clagett et al. | 623/66 |
| 4,137,200 | 1/1979 | Wood et al. | 521/159 |
| 4,237,229 | 12/1980 | Hartdegen et al. | 435/182 |
| 4,241,537 | 12/1980 | Wood | 47/77 |
| 4,343,715 | 8/1982 | Bonaventura et al. | |
| 4,381,332 | 4/1983 | Fulmer et al. | 428/288 |
| 4,517,326 | 5/1985 | Cordts et al. | 523/113 |
| 4,644,033 | 2/1987 | Gnanou et al. | 524/590 |
| 4,670,250 | 6/1987 | Baker | |
| 4,787,976 | 11/1988 | Parham et al. | |
| 4,794,090 | 12/1988 | Parham et al. | 436/531 |
| 4,886,866 | 12/1989 | Braatz et al. | 528/59 |
| 4,919,939 | 4/1990 | Baker | |
| 4,951,657 | 8/1990 | Pfister et al. | |
| 5,023,080 | 6/1991 | Gupta | |
| 5,035,893 | 7/1991 | Shioya et al. | 424/447 |
| 5,079,009 | 1/1992 | Embrey et al. | 424/486 |
| 5,120,816 | 6/1992 | Gould et al. | 623/5 |
| 5,156,601 | 10/1992 | Lorenz et al. | 604/304 |
| 5,160,328 | 11/1992 | Cartmell et al. | 604/304 |
| 5,183,664 | 2/1993 | Ansell | 424/445 |

FOREIGN PATENT DOCUMENTS 1478000  6/1977  United Kingdom.

OTHER PUBLICATIONS

M. E. McNeil et al. "Vaginal Pessaries From Crystalline/Rubbery Hydrogels For The Delivery Of Prostaglandin $E_2$" J. Cont. Rel., vol. 1, 99–117 (1984).

M. V. Bos et al., "Hydrophilic Polyurethanes for the Preparation of Drug Delivery Systems" Acta Pharm. Technol., vol. 33(3), 120–125 (1987).

N. B. Graham et al., "Hydrogels for Controlled Drug Delivery" Biomaterials, vol. 5, 27–36 (1984).

D. R. Knighton, MD et al., "Wound Repair: The Growth Factor Revolution" Chronic Wound Care, Chapter 46, 431–443.

E. R. Edelman et al., "Controlled Release of Basic Fibroblast Growth Factor" DN & P, vol. 4(6), 352–357 (1991).

*Primary Examiner*—Paul B. Prebilic
*Attorney, Agent, or Firm*—Nields & Lemack

[57] ABSTRACT

Controlled release membranes are prepared from polyureaurethane polymer derived from prepolymer units at least 75% of which are oxyethylene-based diols or polyols having essentially all of the hydroxyl groups capped with polyisocyanate are disclosed. The membranes are characterized by their biocompatibility and resistance to nonspecific protein adsorption and are particularly useful for delivery of proteinaceous materials in drug-delivery systems, i.e., wound dressings. Also disclosed are novel biocompatible, protein-nonadsorptive hydrated polymers and the method of producing the same.

27 Claims, No Drawings

PROTEIN NONADSORPTIVE MEMBRANES FOR WOUND DRESSINGS

This application is a continuation of application Ser. No. 07/825,361 filed January 24, 1992, now abandoned.

FIELD OF THE INVENTION

This invention relates to controlled release membranes for drug delivery, and to the process of producing and using the same. More specifically, this invention relates to a protein nonadsorptive, controlled release membrane which is useful as a means of drug delivery in wound dressings. In particular, the membranes of the invention are useful for the delivery of biologically-active materials, i.e., proteins, in wound dressings.

BACKGROUND OF THE INVENTION

Controlled release membranes have been used as a component of drug delivery system in wound dressings. Such membranes are by design permeable to drugs and are capable of controlling the rate at which the drugs are released from the membranes into the wound of a patient. Typically, the membrane is attached to an impermeable backing material by a pressure sensitive adhesive applied over the backing material, or a portion thereof, to attach the composite drug delivery system to the skin of the patient. The exposed surface of the pressure sensitive adhesive is generally covered by a release liner which is removed and discarded when the device is used.

Drugs or medications are defined herein as any biologically-active chemical or natural substance useful for treating a medical or veterinary disorder, or regulating the physiology of a human being or animal. Depending upon the type of drug or medication and the desired release rate, the controlled release membrane has heretofore been a layer of non-porous material such as ethylene vinyl acetate copolymer or crosslinked silicone rubber or a porous polymer-based film. Among the polymer systems selected for this purpose have been the hydrogels. Hydrogels can be defined as polymeric materials which in contact with water can swell but not dissolve due to chemical or physical crosslinkage of the polymer chains.

Typically, hydrogels are formed by polymerizing a hydrophilic monomer in an aqueous solution under conditions such that the prepolymer becomes crosslinked, forming a three-dimensional polymeric network which gels the solution. An example of a crosslinked polymer material derived from polyfunctional prepolymers are the polyurethanes. Polyurethane hydrogels are formed by polymerization of isocyanate-end capped prepolymers to create urea and urethane linkages. Drugs can be physically incorporated into the hydrogel by impregnation of the dried gel with aqueous or organic solutions containing the desired drug.

Representative examples of previously disclosed polyurethane hydrogels include the following: U.S. Pat. No. 4,241,537 (Wood) discloses a plant growth media comprising a hydrophilic polyurethane gel composition prepared from chain-extended polyols; random copolymerization is preferred with up to 50% propylene oxide units so that the prepolymer will be a liquid at room temperature. U.S. Pat. No. 3,939,123 (Matthews) discloses lightly crosslinked polyurethane polymers of isocyanate terminated prepolymers comprised of poly(ethyleneoxy) glycols with up to 35% of a poly(propyleneoxy) glycol or a poly(butyleneoxy) glycol. In producing the Matthews prepolymer, it is taught that the ratio of isocyanato groups to hydroxyl is from about 1.2 to 1.6 equivalents of isocyanato per equivalent of hydroxyl. A solids content of 25 to 40 wt. % is employed in forming the hydrogel. U.S. Pat. No. 4,118,354 (Harada) discloses a polyurethane hydrogel prepared from the reaction product of a polyisocyanate with a polyether which comprises a plurality of alkylene oxides, 50 to 90% by weight of which is ethylene oxide, added at random to a polyalcohol having at least two terminal hydroxyl groups. Harada requires that the prepolymers be liquid or pasty at room temperature in order to avoid having to liquify the prepolymer either by heating it or diluting it with a solvent. U.S. Pat. No. 4,381,332 (Fulmer et al.) discloses a polyurethane gel adhesive to form a nonwoven fabric, prepared from a prepolymer having molecular weight of at least 3000, made from an aliphatic polyisocyanate capped polyether polyol; up to 50% may be butylene oxide and propylene oxide. U.S. Pat. No. 3,719,050 (Asao) teaches a soil stabilization method in which a polyurethane prepolymer having terminal isocyanate groups is injected into the ground; the prepolymer may be diluted with water or may be reacted with water present in or flowing through the soil.

It can be seen that numerous combinations of molecular weights and prepolymer composition have been patented. Typically, prior hydrogel systems have required that the polyols and prepolymers be liquid or pasty at room temperatures to avoid having to melt the composition. This requirement places restraints on the composition of the polyols and prepolymers. As a rule, the prior art teaches copolymerization of propylene oxide or butylene oxide units sufficient to yield liquid polyols and prepolymers. However, inclusion of these monomer units also serves to decrease the hydrophilicity of the prepolymer. Additionally, low molecular weight prepolymers have been used to achieve this end.

In addition, biocompatibility is an increasingly desirable characteristic which would find numerous uses in the health care field if the appropriate properties can be obtained. However, many conventional hydrogels are not taught to be biocompatible.

Finally, prior art polyurethane hydrogels tend to adsorb proteins from solutions with which they are brought into contact. This is a particular problem in attempting to utilize conventional polymers for the preparation of controlled release membranes for delivery of proteinaceous drugs or medicaments.

These problems of biological incompatibility, the lack of hydrophilicity and the tendency to adsorb proteins, have raised significant concerns in the use of traditional controlled release membranes for the delivery of proteinaceous materials, in particular, for a family of proteins called growth factors. In general, proteinaceous drugs are active in minute quantities with disparate effects at different concentrations, and despite advances in recombinant technology, they remain expensive and available in small quantities. In addition, proteinaceous drugs are often not as stable as other medicaments. Prolonged storage may be accompanied by denaturation, degradation or adhesion of proteinaceous materials to the walls of the membranes with actual or effective loss in material or biological activity.

Consequently, there exists a need for polymers or hydrogels, and controlled-release membranes prepared therefrom, which possess improved biocompatibility and increased resistance to protein adsorption.

SUMMARY OF THE INVENTION

The problems of the prior controlled release membranes have been overcome by providing drug permeable, biocompatible, protein nonadsorptive membranes which are highly efficacious for the delivery of proteinaceous materials. Said membranes comprise a permeable, three-dimensional, crosslinked polymeric network prepared from a unique class of hydrophilic polyurethane prepolymers and related polymers characterized by their biocompatibility, their high permeability to various medications, including those of the proteinaceous type, and their ability to resist nonspecific protein adsorption. Wound dressings may be prepared by contacting the membranes with aqueous or organic solutions of a desired medication to physically incorporate or load the drug into the polymeric network of the membrane. The loaded membrane is thereafter associated with an impermeable backing material to contact the membrane to the wound of a patient.

Accordingly, it is a principal object of the present invention to provide an improved controlled release membrane which provides effective and efficient delivery of proteinaceous materials.

It is another object of the present invention to provide a controlled release membrane having a surface which is hydrophilic, transparent and biocompatible and which displays a marked resistance to the adsorption of proteins.

It is also an object of the present invention to provide an improved wound dressing having the membrane of the invention.

It is further an object of the present invention to provide a method of avoiding or minimizing problems heretofore associated with controlled release membranes traditionally used in composite drug delivery systems by providing a controlled release membrane having a hydrophilic, biocompatible, protein nonadsorptive surface.

It is another object of this invention to provide a method of producing a composite drug delivery system especially suited for the delivery of proteinaceous substances.

DETAILED DESCRIPTION OF THE INVENTION

This invention provides a permeable membrane specifically suited for controlling the release of at least one drug or medication. The membrane is comprised of hydrophilic prepolymers and hydrated polyurethane polymers which are covalently extended and crosslinked to provide a three dimensional, polymeric network. The unique biocompatible nature and protein nonadsorptive characteristic of the polymers render the membrane highly efficacious in biomedical applications where sustained delivery of proteinaceous materials is desired.

The prepolymers utilized in this invention are prepared from oxyalkylene-based alcohols. These can be monofunctional alcohols or they can be diols or polyols, including diols or polyols made up of ethylene oxide monomer units. The proportion of ethylene oxide units may vary, and is described in more detail below. Prepolymers are formed when diols and/or polyols are end-capped with di- or polyfunctional isocyanates as described below. One extensive class of hydrophilic, isocyanate-capped urethane prepolymer is described in U.S. Pat. No. 4,137,200 (Wood et al.), the teachings of which are incorporated herein. The Wood et al. prepolymers are blends of a monomeric polyol and polyoxyalkylene glycol, the hydroxyl groups of the blend being capped with a polyisocyanate. The polyoxethylene polyol may have a weight average molecular weight of about 100 to about 20,000, and preferably between about 600 to about 6000, with a hydroxyl functionality of about 2 to 6 or greater, preferably from about 2 to about 8. The polyols should desirably have about 40 to about 100 mole percent ethylene oxide content.

One group of isocyanate-capped urethane prepolymers of this class that can be used in the invention comprises the isocyanate-capped polyesters. Such prepolymers may be made by condensing a polyhydric alcohol with a polycarboxylic acid to form a linear polyester which is then reacted with a slight molar excess of a polyisocyanate to provide an essentially linear polyurethane having terminal isocyanate groups and having an average molecular weight within the range 100 to 20,000, preferably between about 600 to about 6000. Polyhydric alcohols that can be used in preparing such prepolymers include the polyalkylene glycols such as ethylene, propylene and butylene glycol and polymethylene glycols such as tetramethylene and hexamethylene glycols. Another group of isocyanate capped urethane prepolymers that can be used in the invention comprise the isocyanate capped polyethers. These prepolymers can be made by reacting, for example, polyalkylene glycols with diisocyanates of the type listed below to provide a polyurethane having terminal isocyanate groups and having molecular weight within the range 100 to 20,000, preferably between about 600 to about 6000. As specific examples of these prepolymers, the HYPOL™ polyurethane prepolymer series available from Grace Specialty Chemicals Co., W. R. Grace & Co.-Conn., is suitable.

A second class of prepolymers suitable for use in this invention are prepared as described in U.S. Pat. No. 5,039,458, the teaching of which are incorporated herein by reference. The prepolymers comprises polyoxyalkylene diols and polyols which are of generally higher molecular weights and which are predominately or exclusively made up of ethylene oxide monomer units. This second class is somewhat more preferred for use to prepare the membranes of this invention. Preferably, at least 75% of the monomer units should be ethylene oxide, more preferably at least 90%, and most preferably at least 95% up to about 100%. High molecular weight ethylene oxide-based diols and polyols are used to prepare prepolymers and hydrated polymers useful in the present invention. The prepolymers are prepared by reacting the diols or polyols with polyisocyanates at an isocyanate-to-hydroxyl ratio of about 1.8 to about 2.2 so that essentially all of the hydroxyl groups of the polyols are capped with polyisocyanates. The resulting isocyanate-capped prepolymer has an isocyanate concentration of no more than 0.46 milliequivalents per gram. The diol or polyol molecular weight prior to capping with polyisocyanate preferably should be at least about 7000 to 8000 MW, more preferably about 10,000 to about 30,000 MW. A preferred example of suitable prepolymers are prepolymers from the BIOPOL™ polyurethane prepolymer series available from Grace Specialty Chemicals Co., W. R. Grace & Co.-Conn. The hydrated polymers take the form of gel or hydrogels and are included by these terms unless otherwise noted. The term gel or hydrogel are used herein to refer to polymers which are non-foamed in structure.

Aromatic, aliphatic or cycloaliphatic polyisocyanates may be used in any of the above-described embodiments. The use of aliphatic polyisocyanates permits a greater degree of handling and/or shaping since aliphatic isocyanate-capped prepolymers typically require about 20 to 90 minutes to gel to a hydrated polymer state. By contrast, prepolymers capped with aromatic polyisocyanates will gel more rapidly, in about 30 to 60 seconds. In addition, aliphatic polyisocyanates will be preferred when the hydrated polymer is intended to be used in medical applications, because of decreased toxicological considerations. However, hydrated polymers made using aromatic polyisocyanates in the prepolymer are also useful, as well as being suitable for most industrial uses.

Examples of suitable di- and polyfunctional isocyanates are found in the following list:
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene dicyclohexyl diisocyanate
1,4-cyclohexylene diisocyanate
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyante
2,4-dimethyl-1,3-phenylene diisocyante
5,6-dimethyl-1,3-phenylene diisocyanate
2,4-diisocyanatodiphenylether
4,4'-diisocyanatodiphenylether
benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenylmethane
2,6'-dimethyl-4,4'-diisocyanatodiphenyl
2,4-diisocyanatostilbene
3,3'-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate
p,p',p"-triphenylmethane triisocyanate
trifunctional trimer (isocyanurate) of isophorone diisocyanate
trifunctional biuret of hexamethylene diisocyanate
trifunctional trimer (isocyanurate) of hexamethylene diisocyanate
polymeric 4,4'-diphenylmethane diisocyanate The membranes of the invention may be in the form of a flat sheet or a spherical bead, or in any other desired shape useful for drug delivery. In one embodiment, when the membrane is formed as a flat sheet, the membrane is prepared from a casting solution comprising a nonaqueous organic solvent, a hydrophilic, isocyanate capped prepolymer as described hereinabove and a gelling liquid. The term "gelling liquid" is used herein to refer to a liquid which upon contact with the prepolymer will react to polymerize the prepolymer. Suitable gelling liquids include, for example, water or a nonaqueous liquid such as tertiary amines (e.g. triethylamine, triethylenediamine or N-methylimidazole).

The casting solution may also contain a polymerization catalyst or crosslinking agent. Suitable polymerization catalysts include alkyl tin salts wherein the alkyl has 1 to 6 carbon atoms (e.g., dibutyltin dilaurate) and a tertiary amine such as described hereinabove. Suitable crosslinking agents include primary and secondary polyamines and polyfunctional isocyanates. As used herein, "polyfunctional" shall also include "difunctional". Crosslinking agents preferably are employed in stoichiometric or near stoichiometric amounts, although the exact proportions are not critical.

Any nonaqueous solvent which dissolves the prepolymer and does not readily react the prepolymer may be employed in the casting solution. The solvent is preferably an organic solvent and may include among others, tetrahydrofuran, acetone, N-methylpyrolidone, dimethyl formamide, methylene chloride, acetonitrile, alcohols such as 2-propanol, ethanol and methanol can be used if they are dried thoroughly with a suitable drying agent. Polymerization begins to occur spontaneously upon contacting the isocyanate groups of the prepolymer with the gelling liquid. As polymerization begins to occur, gelling takes place and the casting solution is cast onto a support suitable for forming a film or sheet. Following the gelling stage, the solvent is removed by any conventional means, i.e. evaporation, and the resulting sheet is dried to obtain a flat sheet membrane in accordance with the invention. The size of the membrane sheet may vary depending upon the intended use. For example, for use in wound dressings, the membrane sheet may be from about 0.1 to about 5 mm, most preferably about 1.0 to about 2.0 mm.

In a second embodiment, a flat sheet membrane is prepared from a casting solution comprising the hydrophilic, isocyanate-capped prepolymer dissolved in water. As the prepolymer is contacted with water, gelling begins to occur. The casting solution is immediately poured onto a suitable support to form a flat sheet. The film is dried to remove water and recover the membrane. Water cast membranes tend to have a larger pore structure, a higher rate of diffusion, and a higher water content than those membranes prepared hereinabove using nonaqueous gelling solutions.

Spherical beaded membranes of the invention may be prepared by dissolving the prepolymer in a nonaqueous, organic solvent in the presence of a polymerization catalyst such as described hereinabove and slowly adding the prepolymer solution into a large excess of an immiscible liquid phase with mechanical agitation. Preferably, the immiscible liquid phase is silicone oil and the prepolymer solution is added at a volume by volume ratio of about 1:1 to about 1:5 of prepolymer solution to silicone oil. Stable prepolymer beads are recovered by isolation of the beads from the immiscible phase using conventional methodology, i.e. filtration. The beads are thereafter washed with a suitable solvent to remove traces of the immiscible liquid and other impurities and dried using conventional drying techniques. Polymerization catalysts include alkyl tin salts (as described hereinabove) and tertiary amines (e.g. triethylamine, triethylenediamine and N-methylimidazole).

A wide range of sizes of spherical shaped membranes can be produced by varying the spinning rate of the mechanical agitation during mixing of the prepolymer solution/immiscible phase emulsion. In general, the more vigorous the agitation the smaller the size of the spheres. The size of the spheres produced by this process can range from about 5 to about 500 microns in diameter. For use in composite drug delivery systems, i.e. wound dressings, a preferred size range for the spheres is from about 50 to about 200 microns in diameter.

In preparing the membranes of the invention, gelling and curing time will vary, depending in part on the concentration of prepolymer present in the solution from which the hydrated polymer is formed. Gelling time decreases with higher prepolymer concentrations. In addition, gelling time depends on the type of polyisocyanate used in preparing the prepolymer. Aromatic polyisocyanate end-capped prepolymers will gel rapidly, usually reacting in somewhat less than one minute, although the curing time may be longer. Prepolymers capped with aliphatic polyisocyanates have a longer gelling time, typically about 20 to 90 minutes, and may take from up to several hours to several weeks for complete curing. Gelling and curing reaction is also catalyst dependent and will vary depending on the polymerization catalyst used.

When the membrane of the invention is formed as a flat sheet, the casting solution comprises from about 5 to about 50%, more preferably about 10 to about 30%, and most preferably about 10 to about 20% by weight of the urethane prepolymer, from about 10 to 95% by weight of the organic solvent and from about 2 to about 60% by weight of the gelling liquid. When the membrane of the invention is formed as a spherical bead, the prepolymer solution comprises from about 5 to about 50%, more preferably about 20 to about 50%, and most preferably about 20 to about 40% by weight of the urethane prepolymer.

In both flat sheet and spherical bead membrane production, once the membranes are recovered, care should be taken to avoid toxicological problems by eliminating organic solutions and polymerization catalysts before using the membrane in conjunction or contact with patients. Polymerization catalysts and solvents may be removed by washing in water or buffered solutions, i.e., phosphate buffered saline, borated buffer, bicarbonate buffer and the like. The membranes are then dried by methods commonly used in the art, such as by drying after soaking in a water bath. The dried membrane may be rehydrated by contact with aqueous or nonaqueous drug solutions to physically incorporate or "load" the desired medications into the polymeric network of the membrane.

Membranes of the present invention are comprised of hydrated polyurethane polymers which are covalently extended and crosslinked to provide a three-dimensional, polymeric network throughout the membrane. When placed in an environment of use, the loaded membrane releases the drug at a controlled rate by diffusion through the polymeric network. The release rate of a drug will vary depending on the degree of crosslinking in the polymer network. For example, for a given protein, the release rate will be faster from a polymer network with less crosslinking compared to one with more extensive crosslinking.

Polymerization catalysts are used herein in any catalytically effective amount. The term "catalytically effective amount" is used herein to mean any amount sufficient to promote polymerization of the prepolymer to the hydrated crosslinked polymer gel.

The membrane of the invention may be used for the controlled delivery of a variety of organic and inorganic drugs which are either hydrophobic or hydrophilic. Specifically, the membranes of the invention are useful for delivery of proteinaceous materials such as protein growth factors, protein hormones, enzymes, antibodies, lymphokines, cytokines, small peptides and the like. In particular, the membrane of this invention is suitable for the delivery of protein growth factors. Suitable protein growth factors useful herein include, but are not limited to, endothelial cell growth factors (ECGF); epidermal growth factors (EGF); fibroblast growth factors (FGF); hepatocyte growth factors (HGF); nerve growth factors (NGF); platelet-derived growth factors (PDGF); transforming growth factors (TGF), or a combination thereof. For wound dressing, preferred protein growth factors include, but are not limited to, those growth factors capable of regulating wound repair such as PDGF, EGF, TGF, or a combination thereof; most preferably, TGF-Beta and TGF-Alpha growth factors.

The membranes of the invention are useful to produce composite drug delivery systems, i.e. wound dressings, where controlled release of drugs or medications is desired. In accordance with the invention, wound dressings may be prepared by attaching a flat sheet membrane of the invention having the desired medication incorporated therein to all or a portion of an impermeable backing material, i.e., an impermeable polymer, metal foil, or the like. The backing material may be attached to the membrane by any known method, i.e. heat sealing or the use of an adhesive. A pressure sensitive adhesive material is thereafter applied over all or a portion of the membrane to attach the dressing to the wound of the patient. Prior to use, the exposed surface of the pressure sensitive adhesive may be covered by a release liner which is removed and discarded when the device is used.

Drug bearing spherical membranes of the invention may be used as wound dressings by packing the membranes directly into the open wound of a patient. The wound is then contacted with an impermeable backing to hold the spherical membranes in the wound. The impermeable backing may be applied to the wound using a pressure sensitive adhesive, or when the wound is on the patient's limbs, i.e. leg or arm, the backing material may be attached around the limb by tying or using conventional fastening mechanisms.

The surface properties of the hydrated polymer membranes described herein are unique and offer significant advantages over conventional hydrogel controlled-release membranes. In particular, the surface of the membranes of this invention is resistant to nonspecific protein adsorption. The protein nonadsorption properties of the membrane surface allows for delivery of protein based medication in physiologically effective amounts by minimizing the loss of material and biological activity due to adhesion of proteins to the walls of the membranes. Thus, the membranes of this invention are particularly useful for delivery of proteinaceous drugs in which conventional polymers and hydrogels are unacceptable or undesirable because of protein adsorption.

The hydrophilicity and the biocompatibility of the surfaces of the membranes of this invention prohibit or inhibit denaturation or degradation of proteins during prolonged storage. The biocompatibility of the membranes is related, at least in part, to the ability of the membrane surface to resist protein adsorption. While not limiting the effectiveness of this invention to any specific theory, the unique qualities of these membranes are believed to relate to the use of predominantly or exclusively ethylene oxide-based diols or polyols in the formulation of the prepolymers and hydrated polymers. When the membranes of this invention are used in contact with an aqueous system, the ethylene oxide segments of the polymer attract and complex with water molecules. Consequently, the surface presented to living cells or tissues is predominantly a layer of water. This protective curtain of water renders the underlying synthetic polymeric material noninteractive with proteins. The result is a hydrated polymer surface which is physiologically acceptable, and which does not adsorb or denature proteins from the environment in which the polymer is used.

Biocompatibility, as used herein to describe the hydrated polymers of this invention, refers to the resistance to adsorption of protein and to the lack of interactiveness with physiological surfaces, as discussed above. In addition, the hydrated polymer membranes of this invention have been demonstrated to be nontoxic to mammalian cells. Use of aliphatic polyisocyanates in preparation of the prepolymers may further enhance the biocompatibility of the membranes since the potential degradation products of aliphatic polyisocyanates are reported to be significantly less carcinogenic than those of aromatic isocyanates. However, if aromatic polyisocyanates are used, careful washing or other means for removing any unreacted isocyanate and related aminecontaining by-products generally will be sufficient to render the hydrated polymer membranes biocompatible.

The hydrated polymer membranes of this invention are covalently extended and crosslinked and therefore are not readily soluble or degradable in aqueous systems under physiological conditions, which further increases the membranes' suitability for use with living cells or tissues. The physical integrity of the hydrated polymer is maintained when used in an aqueous system, eliminating problems with toxicity and contamination. Moreover, these characteristics make it possible to use the hydrated polymer membranes of this invention in aqueous systems over extended periods with minimal loss of polymer strength or integrity.

The invention is further detailed by the following examples. The examples are given to illustrate the invention and are not meant to limit the invention described herein.

EXAMPLE I (BIOPOL™ XP-5 Film Membrane Using Tetrahydrofuran)

A flat sheet membrane of the invention was prepared by mixing 80 g of BIOPOL™ XP-5, a urethane prepolymer obtained from W. R. Grace & Co.-Conn., 184 g of tetrahydrofuran, 2.0 g of triethylenediamine catalyst and 4.0 g of water. Immediately after preparing the casting solutions, 60 g of the solution was poured into a 9"×13" cake pan and sealed over nitrogen. After gelling, the solvent was evaporated at 70° C. and the film was reheated to provide a film approximately 50 mils (0.050 inches) thick in hydrated form.

EXAMPLE II (BIOPOL™ XP-10 Film Membrane Using Borax-Saturated Acetone)

A flat sheet membrane of the invention was prepared by mixing together 16 g of a 25% solution of BIOPOL™ XP-10 in acetone, a urethane prepolymer obtained from W. R. Grace and Co.-Conn., 5 g of borax-saturated acetone (decanted from a bottle of acetone where borax was present in excess and was settling on the bottom of the container) and 1.0 g of an aqueous solution of 0.38% by weight of borax in water. 18.8 g of the above solution was poured into a 9 cm flat-bottomed crystallizing dish and was placed in a sealed bag over nitrogen. After the mixture gelled, the acetone was evaporated in a forced-air oven at 70° C.

EXAMPLE III (Preparation of HYPOL™ 6200 Film Membrane Using Acetone)

A flat sheet membrane was prepared by mixing 40 g of HYPOL™ 6200, a urethane prepolymer obtained from W. R. Grace & Co.-Conn., 92 g acetone and 1.0 g water. The mixture was poured into a 9"33 12" cake pan over nitrogen. The mixture gelled in approximately 60 minutes. Acetone was evaporated in a forced-air oven at 70° C. and the film was recovered. After several days of hydration, the hydrated material contained 81% water at room temperature.

EXAMPLE IV (Preparation of BIOPOL™ XP-5 Bead Membrane Catalyzed by Triethylamine)

Silicone oil (20 gm) was placed in a 600 ml beaker and rotated on an orbital shaker at 200 rpm. To this a solution was slowly added which contained 10 gm BIOPOL™ XP-5 (lot #1710) and 3.2 ml triethylamine in 10 gm tetrahydrofuran. The rotary mixing was continued for 17 hr at room temperature. At the end of this period, clear, stable beads, ≈100–200μ in diameter, could be isolated from the oil by filtration.

EXAMPLE V (Preparation of BIOPOL™ XP-5 Beads Catalyzed by N-methyl imidazole)

Example IV was repeated with the exception that triethylamine was replaced with 2.4 ml of N-methyl imidazole. Stable beads of similar size were again isolated after a 17 hour mixing period.

EXAMPLE VI (Preparation of Beads using HYPOL™ 6200)

Silicone oil (80.6 gm) and Dow Corning Silicone Surfactant #190 (0.9 gm) were added to a 600 ml beaker and shaken on an orbital shaker at 200 rpm. To this was slowly added a solution which contained 16.8 gm HYPOL® 6200, a urethane prepolymer obtained from W. R. Grace & Co.-Conn., 21.3 gm tetrahydrofuran and 3.6 gm triethylamine. After shaking for 17 hours, the suspension was diluted with 120 ml tetrahydrofuran. The beads were collected by filtration and washed with 2-propanol. The resulting beads were white, very tough, and about 200μ in diameter.

EXAMPLE VII (Preparation of Water Cast Film Membrane)

Water-cast films of BIOPOL polymer were prepared by dissolving BIOPOL XP-5 prepolymer in an excess of water according to the proportions specified. For example, a 1:5 formulation would contain 1.0 gm BIOPOL XP-5 and 5.0 gm water. Immediately after the addition of water to the prepolymer the mixture was stirred vigorously until all the prepolymer was in solution. After a period of 30 to 60 minutes the solution became a semi-solid gel. The gel was air-dried under ambient conditions for 17 hours, then in a vacuum oven at 40° C. for 48 hours. Small pieces were cut and weighed then stored until ready for use.

EXAMPLE VIII (Insulin release from BIOPOL™ XP-5 Membrane)

Varying amounts of bovine pancreatic insulin were placed in 1.0 cc PBS (phosphate-buffered saline) and added to 1 cm$^2$ pieces of dry BIOPOL™ XP-5 films prepared as described in Example I. The film pieces were allowed to hydrate to absorb the protein for 19 hours at room temperature. Essentially all the liquid was taken up, and the films swelled to about 4 times their original size. Two cc of PBS were added to each swollen gel and replaced after 4.75 hours. Samples were removed at different times and protein content was determined using the dye-binding procedure of Bradford (M. M. Bradford, Anal. Biochem., 72, 248 (1976). The amount of insulin cumulatively recovered as a function of time was as follows:

| Amount of Insulin | Total Insulin Recovered (μg) after | | | |
|---|---|---|---|---|
| Added to Gel, μg | 2 hrs | 4.75 hrs | 5.75 hrs | 3 days |
| 100 | 25 | 31 | 37 | 58 |
| 500 | 180 | 231 | 270 | 320 |

EXAMPLE IX (Transforming Growth Factor Alpha (TGF-α) Release from BIOPOL Membrane)

To a dried piece of organic solvent-cast BIOPOL™ XP-5 hydrogel film (10×10 mm, 136 mg) was added 0.92 ml of PBS (phosphate-buffered saline) containing 124.6 μg TGF-α. After 2 days, a brief wash of the film removed 47 μg TGF-α as determined by high pressure liquid chromatography analysis. One cc PBS was added and replaced at various times to permit diffusion. The amount of protein recovered at these times was as follows:

| Hours of Diffusion | Total TGF-α Recovered, μg |
|---|---|
| 3.5 | 20.0 |
| 5 | 35.6 |
| 7 | 35.6 |
| 24 | 35.6 |

At the end of this experiment, the membrane, which originally weighed 136 mg, weighed 1.0960 gm, which corresponds to a water content of 87.6%.

EXAMPLE X (Release of Chymotrypsinogen from Water Cast BIOPOL™ Membrane) XP-5 Hydrogel (16089-73)

Four water cast BIOPOL™ XP-5 flat sheet membranes were prepared as in Example VII by mixing 1 part BIOPOL™ XP-5 prepolymer, a urethane obtained from W. R. Grace and Co.-Conn., with 5, 10, 15 and 20 parts of water. Small pieces of each membrane, 0.3–0.6 gm wet weight, were dried thoroughly. To each was added 0.20 ml of 5 mg/ml Chymotrypsinogen A in PBS (phosphate-buffered saline). These were allowed to absorb at 4° C. for 3 days. After brief washes, the membranes were incubated in 1 cc PBS which was replaced at various times. The amount of protein recovered in each fraction was determined using the dye-binding procedure of Bradford, as in Example VIII. The results were as follows:

| Hours of Diffusion | Total Chymotrypsinogen Recovered (μg) from Gels | | | |
|---|---|---|---|---|
| | 1:5 | 1:10 | 1:15 | 1:20 |
| 0 (Combined Washes) | 1041[1] | 517 | 345 | 394 |
| 2 | 179 | 326 | 317 | 320 |
| 4 | 54 | 167 | 174 | 134 |
| 6 | 37 | 56 | 85 | 69 |
| 24 | 39 | 17 | 73 | 43 |
| Recovery | 131.1% | 108.3% | 99.4% | 96.0% |

[1]This value is probably an overestimate

We claim:

1. A wound dressing comprising a hydrophilic, biocompatible, protein nonadsorptive, controlled release membrane, wherein said membrane consists essentially of a permeable, three dimensional, crosslinked, polymeric network of a hydrated polyurea-urethane polymer hydrogel derived from prepolymer units at least 75% of which are oxyethylene-based diols or polyols having an average molecular weight of about 10,000 to about 30,000, said diols or polyols having essentially all of the hydroxyl groups capped with polyisocyanate; and a drug incorporated into said polymeric network of said membrane in an amount effective for treating wounds.

2. The wound dressing of claim 1 wherein the wound dressing is a flat sheet membrane.

3. The wound dressing of claim 1 wherein the wound dressing is a spherical particulate membrane.

4. The wound dressing of claim 2 wherein the wound dressing is prepared from a casting solution comprising (a) the isocyanate capped urethane prepolymer, (b) an organic solvent that will dissolve the prepolymer and will not readily react with the prepolymer and (c) a gelling liquid.

5. The wound dressing of claim 4 wherein the gelling liquid is selected from water or a tertiary amine.

6. The wound dressing of claim 5 wherein the gelling liquid is a tertiary amine selected from triethylamine, triethylenediamine or N-methylimidazole.

7. The wound dressing of claim 4 wherein the casting solution comprises from 5 to 50% by weight of the urethane prepolymer, from 10 to 95% by weight of the organic solvent and from 2 to 60% by weight of the gelling liquid.

8. The wound dressing of claim 4 wherein the casting solution further comprises a polymerization catalyst selected from the group consisting of inorganic salts and tertiary amine.

9. The wound dressing of claim 8 wherein the polymerization catalyst is a tertiary amine selected from triethylamine, triethylenediamine or N-methylimidazole.

10. The wound dressing of claim 3 in which the membrane is prepared by (1) placing the isocyanate-capped urethane prepolymer in a nonaqueous organic solvent in the presence of a polymerization catalyst to form a polymer gel solution;

(2) adding the polymer gel solution to an immiscible liquid phase with stirring to form spherical particulate membranes; and (3) recovering the particulate membranes from the immiscible liquid phase.

11. The wound dressing of claim 10 in which the immiscible liquid phase is silicone oil.

12. The wound dressing of claim 10 in which the polymerization catalyst is selected from the group consisting of alkyl tin salts and tertiary amines.

13. The wound dressing of claim 12 wherein the polymerization catalyst is a tertiary amine selected from triethylamine, triethylenediamine or N-methylimidazole.

14. A controlled drug delivery system comprising in combination:

(a) an impermeable backing member;

(b) a controlled release membrane of claim 1 positioned next to said backing member;

(c) a means to attach said drug delivery system to the wound of a patient; and (d) optionally, a release liner releasably attached to said controlled release membrane.

15. The drug delivery system of claim 14 wherein the drug is a protein selected from the group consisting of protein growth factors, protein hormones, enzymes, antibodies, lymphokines, cytokines and small peptides.

16. The drug delivery system of claim 15 wherein the protein is a protein growth factor.

17. The drug delivery system of claim 16 wherein the protein growth factor is an endothelial cell growth factor, and epidermal growth factor, a fibroblast growth factor, a hepatocyte growth factor, a nerve growth factor, a platelet-derived growth factor, a transforming growth factor, or a combination thereof.

18. The drug delivery system of claim 15 wherein the controlled release membrane is in the form of a flat sheet.

19. The drug delivery system of claim 15 wherein the controlled release membrane is in the form of a spherical particle.

20. The drug delivery system of claim 15 wherein the controlled release membrane is attached to said backing member.

21. A method of promoting the healing of wounds in humans comprising applying to the wound of a patient a drug releasing wound dressing as described in claim 1.

22. The method of claim 21 wherein the drug is a protein selected from the group consisting of protein growth factors, protein hormones, enzymes, antibodies, lymphokines, cytokines and small peptides.

23. The method of claim 21 wherein the drug is at least one protein growth factor.

24. The method of claim 23 wherein the protein growth factor is an endothelial cell growth factor, an epidermal growth factor, a fibroblast growth factor, a hepatocyte growth factor, a nerve growth factor; a platelet-derived growth factor, a transforming growth factor, or a combination thereof.

25. The method of claim 21 wherein the controlled release membrane is in the form of a flat sheet.

26. The method of claim 21 wherein the controlled release membrane is in the form of a spherical particle.

27. The method of claim 21 wherein the controlled drug delivery system is applied to the wound of the patient with an adhesive.

* * * * *